United States Patent
Stearns et al.

(10) Patent No.: US 9,546,646 B2
(45) Date of Patent: Jan. 17, 2017

(54) PUMP AND INJECTOR FOR LIQUID CHROMATOGRAPHY

(71) Applicant: Valco Instruments Company, L.P., Houston, TX (US)

(72) Inventors: Stanley D. Stearns, Houston, TX (US); Ales Plistil, Houston, TX (US)

(73) Assignee: Valco Instruments Company, L.P., Houston, TX (US)

( * ) Notice: Subject to any disclaimer, the term of this patent is extended or adjusted under 35 U.S.C. 154(b) by 197 days.

(21) Appl. No.: 14/156,197

(22) Filed: Jan. 15, 2014

(65) Prior Publication Data

US 2014/0197247 A1    Jul. 17, 2014

Related U.S. Application Data

(60) Provisional application No. 61/753,299, filed on Jan. 16, 2013.

(51) Int. Cl.
  *G01N 30/20* (2006.01)
  *F04B 19/00* (2006.01)
  *F04B 7/00* (2006.01)
  *F04B 13/00* (2006.01)

(52) U.S. Cl.
  CPC ........... *F04B 19/006* (2013.01); *F04B 7/0007* (2013.01); *F04B 13/00* (2013.01); *G01N 30/20* (2013.01)

(58) Field of Classification Search
  CPC .............. G01N 30/20; G01N 2030/201; G01N 2030/202; F04B 13/00; F04B 7/0007

USPC ......... 239/91; 277/650–654; 29/890.122, 12, 29/888.44, 890.142

See application file for complete search history.

(56) References Cited

U.S. PATENT DOCUMENTS 4,300,393 A    11/1981 Stearns
4,444,066 A    4/1984 Ogle et al.
(Continued)

FOREIGN PATENT DOCUMENTS

WO    2012095097 A1    7/2012
WO    2012122442 A2    9/2012
WO    2012122442 A3    10/2013

OTHER PUBLICATIONS

Blaine R. Copenheaver, Notification of Transmittal of the International Search Report and the Written Opinion of the International Searching Authority, or the Declaration—PCT/US2014/011697, Aug. 13, 2014, 1 page, United States Patent & Trademark Office as International Search Authority, Alexandria, Virginia 22313 USA.

(Continued)

*Primary Examiner* — Arthur O Hall
*Assistant Examiner* — Chee-Chong Lee

(57) ABSTRACT

A combined pump-injector valve utilizing a single piece as the barrel of the pump and as the stator of the valve, thus eliminating any need for connections between a pump and a valve, and therefore the potential for high-pressure leaks or pressure reductions. The combined pump-injector valve permits injection of nanoliter-sized samples into a chromatographic column, which is sealed during loading of the sample and filling of the pump, such that complete analyses can be completed with microliters of mobile phase with nanoliters of a sample.

17 Claims, 13 Drawing Sheets

(56) References Cited

U.S. PATENT DOCUMENTS

| | | | | |
|---|---|---|---|---|
| 4,957,085 | A * | 9/1990 | Sverdlin | F02M 47/043 123/41.31 |
| 5,004,416 | A * | 4/1991 | Van Den Brink | B29C 45/281 251/229 |
| 5,948,448 | A * | 9/1999 | Schmidt | B29C 45/281 425/192 R |
| 6,155,123 | A | 12/2000 | Bakalyar | |
| 7,517,395 | B2 * | 4/2009 | Logan | G01N 30/18 277/652 |
| 2011/0129561 | A1 * | 6/2011 | Adas | B29C 45/2806 425/564 |
| 2011/0244070 | A1 * | 10/2011 | Schmidt | B29C 45/281 425/557 |
| 2011/0270167 | A1 * | 11/2011 | Matusch | A61J 1/2096 604/89 |
| 2013/0323103 | A1 * | 12/2013 | Shreve | F04B 1/0448 417/437 |
| 2013/0340609 | A1 * | 12/2013 | Shreve | F04B 13/00 92/165 R |

OTHER PUBLICATIONS

Blaine R. Copenheaver, International Search Report—PCT/US2014/011697 and search History, Aug. 13, 2014, 4 pages, United States Patent & Trademark Office as International Search Authority, Alexandria, Virginia 22313 USA.

Blaine R. Copenheaver, Written Opinion of the International Searching Authority—PCT/US2014/011697, Aug. 13, 2014, 9 pages, United States Patent & Trademark Office as International Search Authority, Alexandria, Virginia 22313 USA.

William Krynski, Notification of the Transmittal of International Preliminary Report on Patentability—PCT/US2014/011697, Jan. 9, 2015, 1 page, United States Patent & Trademark Office as International Search Authority, Alexandria, Virginia 22313 USA.

William Krynski, International Preliminary Report on Patentability—PCT/US20141011697, Jan. 6, 2015, 10 page, United States Patent & Trademark Office as International Search Authority, Alexandria, Virginia 22313 USA.

Olona Laglera, Extended European Search Report—14740712.6, Aug. 8, 2016, 7 pages, European Patent Office, Munich, Germany.

* cited by examiner

PUMP AND INJECTOR FOR LIQUID CHROMATOGRAPHY

CROSS-REFERENCE TO RELATED APPLICATIONS

This application claims the benefit of U.S. Provisional Patent Application No. 61/753,299 entitled "Integral nano-scale pump and injector for high performance liquid chromatography" filed on Jan. 16, 2013 in the United States Patent and Trademark Office and which is incorporated herein by reference.

STATEMENT REGARDING FEDERALLY SPONSORED RESEARCH OR DEVELOPMENT

Not Applicable.

BACKGROUND OF THE INVENTION

1. Field of Invention

The present invention pertains to pump and injection valve systems for use with liquid chromatography. More particularly, the present invention pertains to a combined pump/injection valve for injection of a nanoliter-sized sample into a chromatography column utilizing an single piece as the barrel of the pump and as the stator of the valve, thus eliminating any need for connections between the pump and valve.

2. Description of the Related Art

High performance liquid chromatography (HPLC) is generally performed using pumps, columns and injection valves scaled to deliver fluids at flow rates measured in cubic centimeters of fluid per minute. These components are typically separate and joined together to provide a system for HPLC. Unfortunately, these systems require relatively large sample volumes, large mobile phases, and large flow rates for analysis.

Additionally, these relatively large systems frustrate generate of field portable HPLC units, where there is a need for a lightweight robust flow system which uses a minimum of mobile phase during an analysis.

It would therefore be desirable to provide an integrated nano-scale pump and injection valve for high performance liquid chromatography.

SUMMARY OF THE INVENTION

The present invention therefore meets the above needs and overcomes one or more deficiencies in the prior art by providing a combined pump/injector valve which injects nanoliter samples into a chromatographic column, which is sealed during loading of the sample and filling of the pump, such that complete analyses can be completed with microliters of mobile phase, ranging from as small as about 5-10 nanoliters, to 60 nanoliters, and larger. The present invention therefore provides a lightweight robust flow system which uses a minimum of mobile phase during an analysis and is appropriate for use as a field portable HPLC unit.

The present invention provides an integral nano-scale pump and injection valve for high performance liquid chromatography which includes an integrated barrel-stator, which has an elongate barrel in a first end and a stator at a second end, a plunger slidably disposed within an interior chamber of the barrell of substantially uniform cross-section, and a rotor, wherein the pump and injection valve is switchable between a load position and a injection position.

In one embodiment, the circular rotor has a surface adjacent the stator and has a plurality of channels in its surface and is with respect to the stator about a centerpoint between the load position and the injection position. The elongate barrel portion of the integrated barrel-stator includes an open ends, a length, and a sidewall defining the interior chamber adapted to receive a supply of fluid, an outer diameter, and a wall thickness. The circular stator has an orifice therethrough at its centerpoint and a first side and a second side such that the elongate barrel open distal end is aligned with the second side of the stator at the centerpoint and the interior chamber includes the orifice. The pump is therefore in communication with the valve at the orifice.

In a first embodiment, the rotor includes three channels and the stator has a first stator port for communication with a mobile phase supply, a second stator port in communication with a fifth stator port, a third stator port for communication with a sample reservoir, a fourth stator port for sample outflow, a sixth stator port for communication with a chromatography column, a seventh stator port for return from the chromatography column, and an eighth stator port for outflow from the valve. In the first embodiment, the load position is defined by the first port and the orifice communicating with a first channel and by the third port and the fourth port communicating with a second channel. In the first embodiment, the injection position is defined by the orifice and the second port communicating with the first channel, by the fifth port and the sixth port communicating with the second channel, and by the seventh port and the eighth port communicating with the third channel.

In the alternative embodiment, the rotor includes four channels and the stator has a first stator port for communication with a mobile phase supply, a second stator port in communication with a fifth stator port via an external loop, a third stator port for communication with a sample reservoir, a fourth stator port for sample outflow, a sixth stator port for communication with a chromatography column, a seventh stator port for return from the chromatography column, and an eighth stator port for outflow from the valve. In the alternative embodiment, the load position is defined by the first port and the orifice communicating with a first channel, by the second port and the third port communicating with the second channel, and the fourth port and the fifth port communicating with the third channel. In the alternative embodiment, the injection position is defined by the orifice and the second port communicating with the first channel, by the fifth port and the sixth port communicating with the third channel, and by the seventh port and the eighth port communicating with the fourth channel.

In a further alternative embodiment, where the embodiment is used as a pump without regard to the equipment connected thereto, the rotor has only one channel and the stator has a first stator port for communication with a mobile phase supply and a second stator port for communication with an external device. In the further alternative embodiment, the load position is defined by the first port and the orifice communicating with a first channel and the injection position is defined by the orifice and the second port communicating with the first channel.

In an additional alternative embodiment, wherein the the embodiment is used to push sample through a column, but wherein the output of the column is provided to other equipment rather than through the valve, the embodiment includes channels and the stator has a first stator port for communication with a mobile phase supply, a second stator port in communication with a fifth stator port via an external loop, a third stator port for communication with a sample reservoir, a fourth stator port for sample outflow, and a sixth stator port for communication with a chromatography column. In the additional alternative embodiment, the load position is defined by the first port and the orifice communicating with a first channel, by the second port and the third port come communicating with the second channel, and the fourth port and the fifth port communicating with the third channel. In the alternative embodiment, the injection position is defined by the orifice and the second port communicating with the first channel, and by the fifth port and the sixth port communicating with the third channel.

Additional aspects, advantages, and embodiments of the invention will become apparent to those skilled in the art from the following description of the various embodiments and related drawings.

BRIEF DESCRIPTION OF THE DRAWINGS

So that the manner in which the described features, advantages, and objects of the invention, as well as others which will become apparent are attained and can be understood in detail; more particular description of the invention briefly summarized above may be had by referring to the embodiments thereof that are illustrated in the drawings, which drawings form a part of this specification. It is to be noted, however, that the appended drawings illustrate only typical preferred embodiments of the invention and are therefore not to be considered limiting of its scope as the invention may admit to other equally effective embodiments.

In the drawings.

DESCRIPTION OF THE PREFERRED EMBODIMENT

Figure 2:
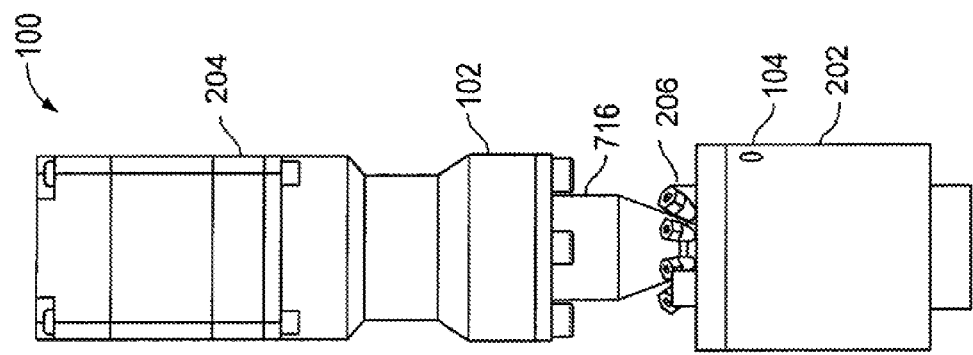
FIG. 2 is an illustration of a side view of one embodiment of the present invention as assembled.
Figure 1:
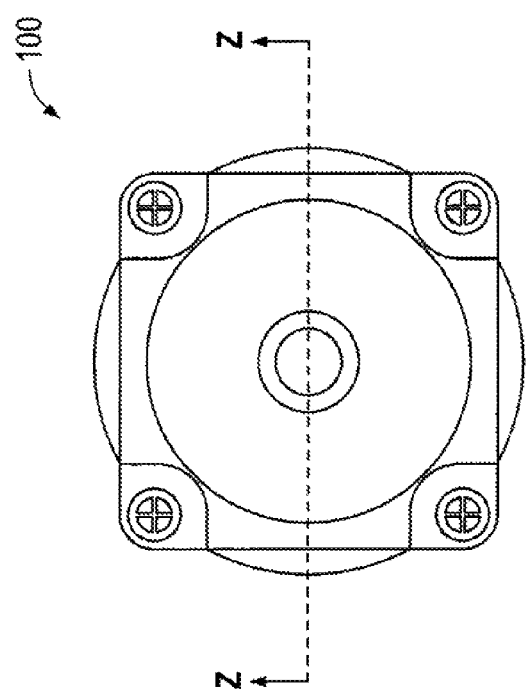
FIG. 1 is an illustration of a top view of one embodiment of the present invention as assembled.

Referring to FIGS. 1 and 2, a two-position embodiment of the integrated nano-scale pump and injection valve 100 is provided. A top view of one embodiment of the integrated nano-scale pump and injection valve 100 as assembled is provided in FIG. 1 while a side view is provided FIG. 2. As illustrated in FIGS. 1B and 2, the integrated nano-scale pump and injection valve 100 includes an integrated barrel-stator 716 which provides the interface between the pump section 102 and valve section 104.

Figure 3:
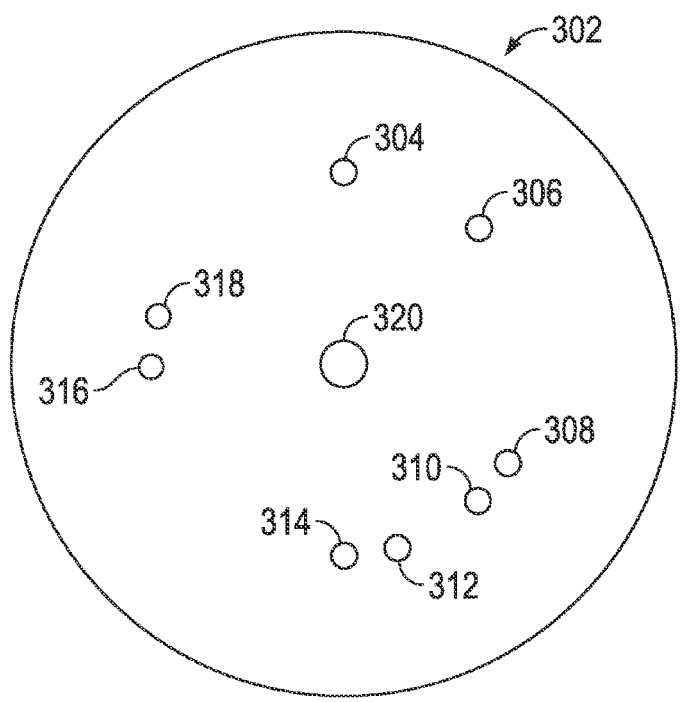
FIG. 3 is an illustration of the face of the stator of the integrated barrel-stator of the first embodiment of the present invention.
Figure 4:
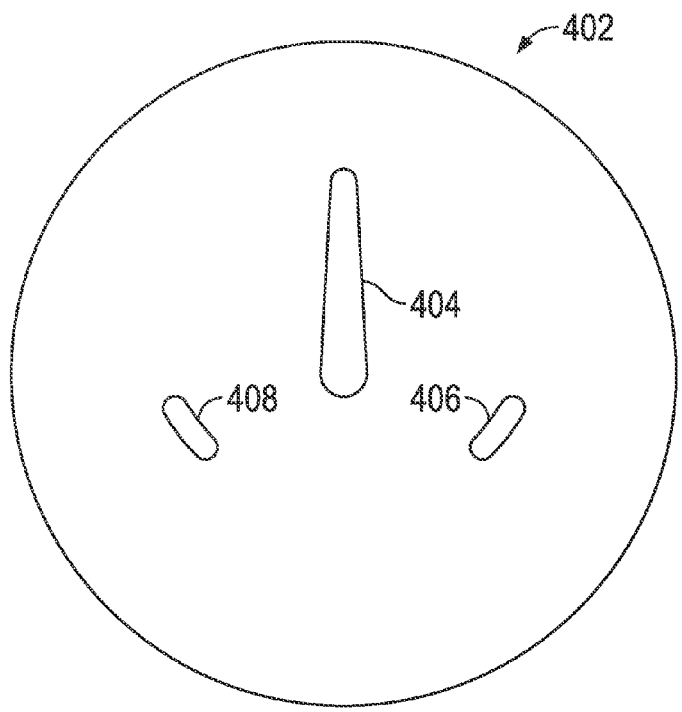
FIG. 4 is an illustration of the face of the rotor of the first embodiment of the present invention.
Figure 13:
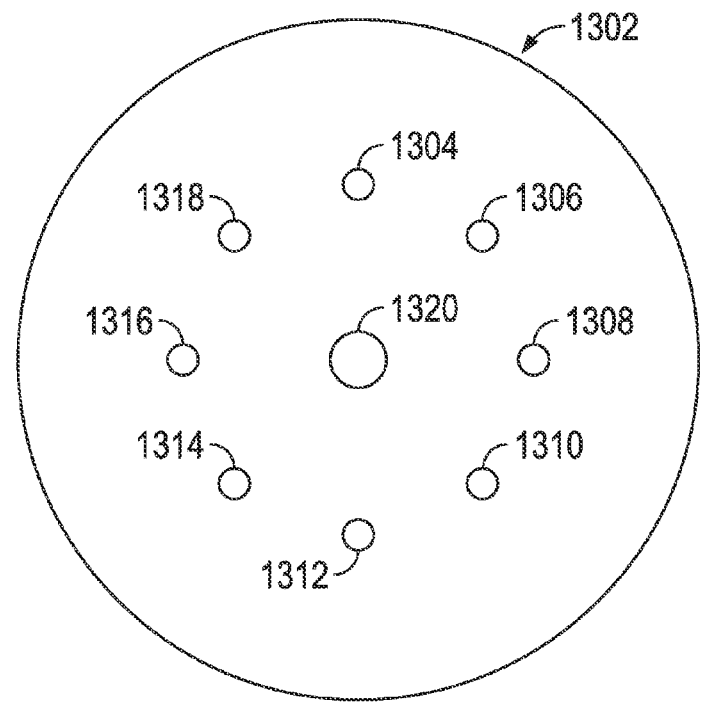
FIG. 13 is an illustration of the face of the stator of the integrated barrel-stator in the alternative embodiment of the present invention.
Figure 14:
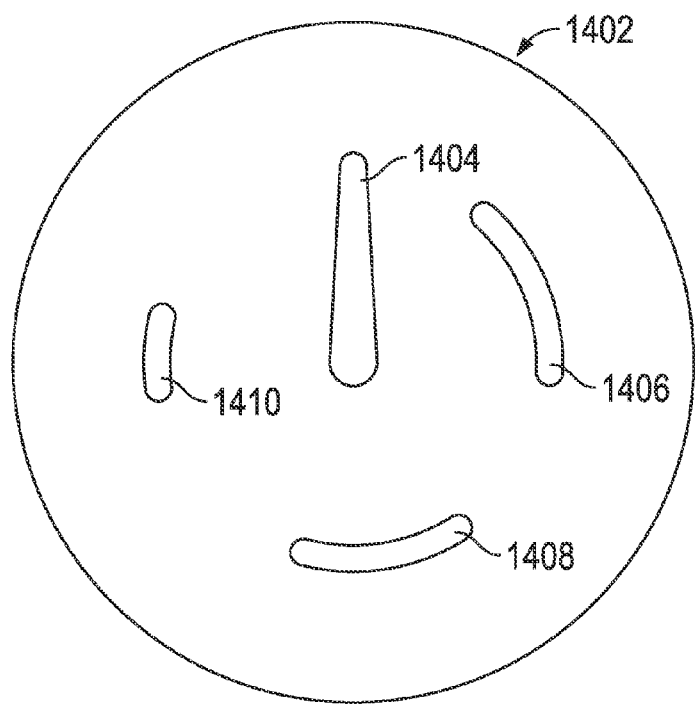
FIG. 14 is an illustration of the face of the rotor of the alternative embodiment of the present invention.

Referring to FIGS. 3 and 4, constructions of the face of the stator 302 and the face of the rotor 402 of the integrated barrel-stator 716 are illustrated for a first embodiment. Referring to FIGS. 13 and 14, constructions of the face of the stator 302 of the integrated barrel-stator 716 and the face of the rotor 1402 of the valve section 104 are illustrated for an alternative embodiment.

Referring to FIGS. 1-22, by forming the elongate barrel 726 of the pump 708 and the stator 302, 1302, 1712, 1932 of the valve 710 of a single part as integrated barrel-stator 716, the integrated nano-scale pump and injection valve 100 may operate at high pressures without degradation incident to intervening parts and fittings.

Unlike the prior art where a valve and pump were separate bodies simply joined together, in the integrated nano-scale pump and injection valve 100, as illustrated in FIGS. 7-12B, the elongate barrel 726 of the pump 708 and the stator 302, 1302, 1712, 1932 of the valve 710 are integrally formed of a single piece to provide direct communication between the pump 708 and the valve 710 without introducing any fittings or connectors which may swell or leak during high pressure operation.

By switching between the maximum extent of the load position 502, 1502, 1710, 1928 and the maximum extent of the injection position 602, 1602, 1802, 2002, the integrated nano-scale pump and injection valve 100 provides a pump 708, which may be sized to hold microliters for use with nano-scale columns for quick separation.

Upon initiation of loading, the pump 708 and valve 710 and positioned in the load position 502 and the plunger 706 begins being retracting by the piston 712 and draws a solvent from a reservoir, such as through a 15 cm×200 μm steel tube into the barrel 726. At the same time and independent of pump filling, a sample is introduced into the sample loop through a 5.08 cm×75 μm inner diameter capillary, which is connected to the port 308 on the pump and to a sample supply, preferably using a zero-dead volume connector.

After completion of loading, the integrated nano-scale pump and injection valve 100 may be switched for injection, changing the direction of operation of the pump 708 and changing the position of the valve 710. During injection, the plunger 706 is driven by the piston 712 into the barrel 726. The rate of advance, and therefore the dispensing flow rate, may be controlled by power supply and/or by computer software. As the plunger 706 is driven forward by the piston 712, the sample is driven from the sample passage of second channel 406 into the column 504 while the mobile phase flows from the barrel 726 through the loop 506, through the column 504 and to the detector.

Figure 5:
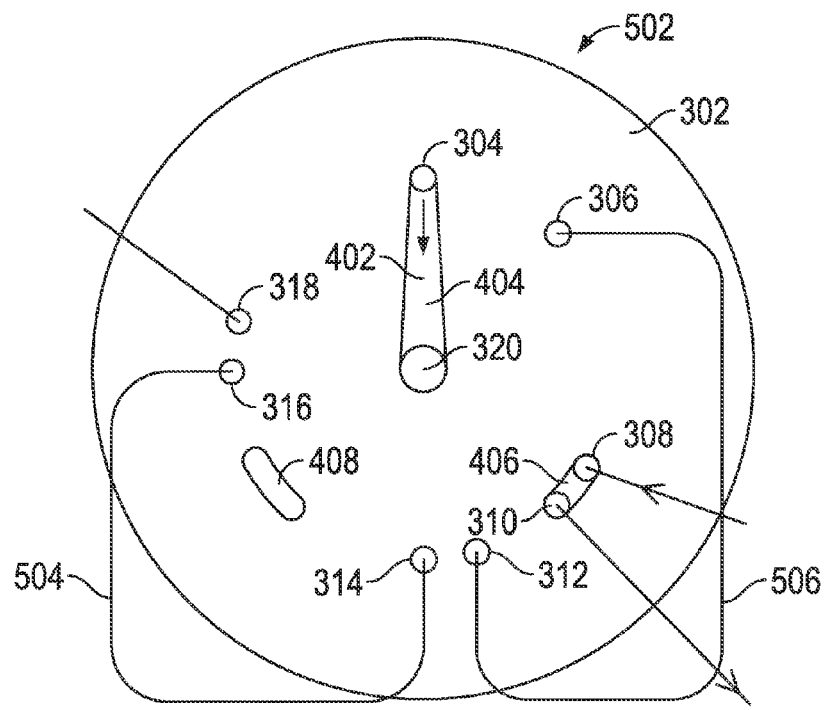
FIG. 5 is an illustration of the relative positions of the face of the stator and the face of the rotor of the first embodiment of the present invention in the load position.
Figure 7:
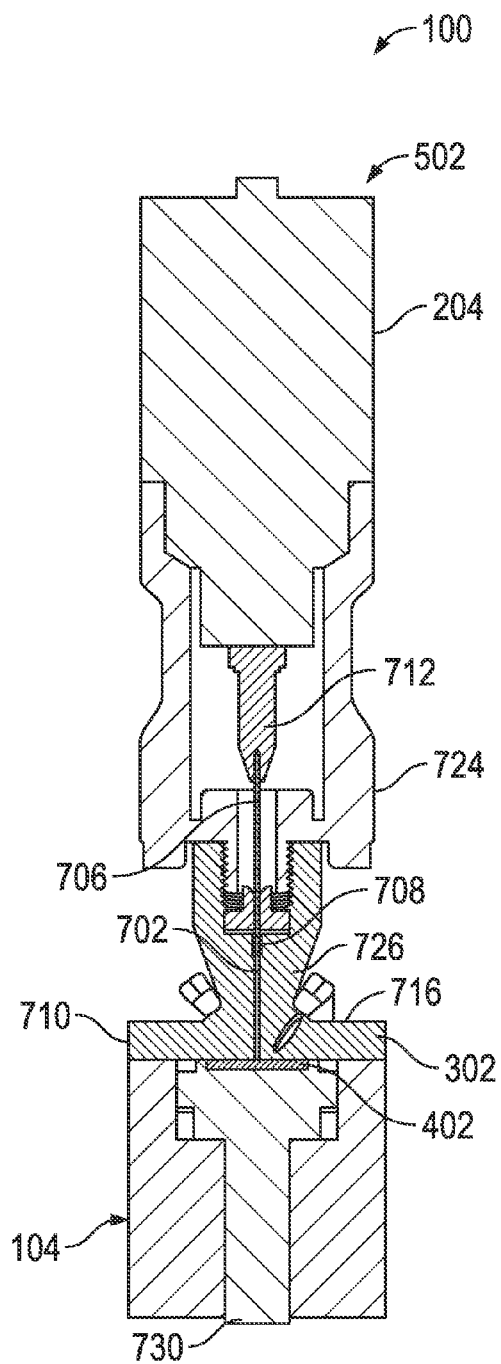
FIG. 7 is a cross-section illustration of the present invention along line Z-Z of FIG. 1 for the maximum position of the pump associated with the load position in connection with a linear actuator.
Figure 10:
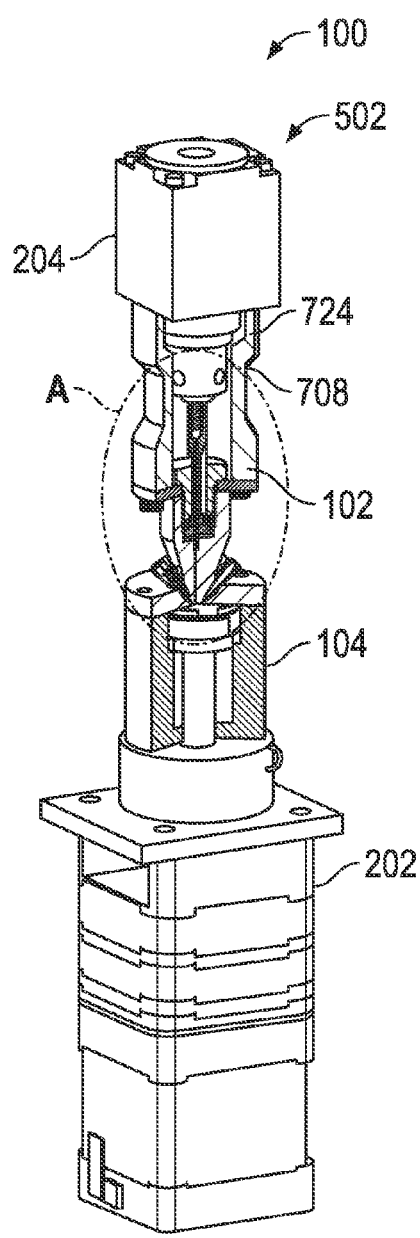
FIG. 10 is an illustration of isometric view of the embodiment of the present invention with the pump and valve actuators illustrating the first valve position illustrated in FIGS. 5 and 7 at the maximum position of the pump in the load position.
Figure 11:
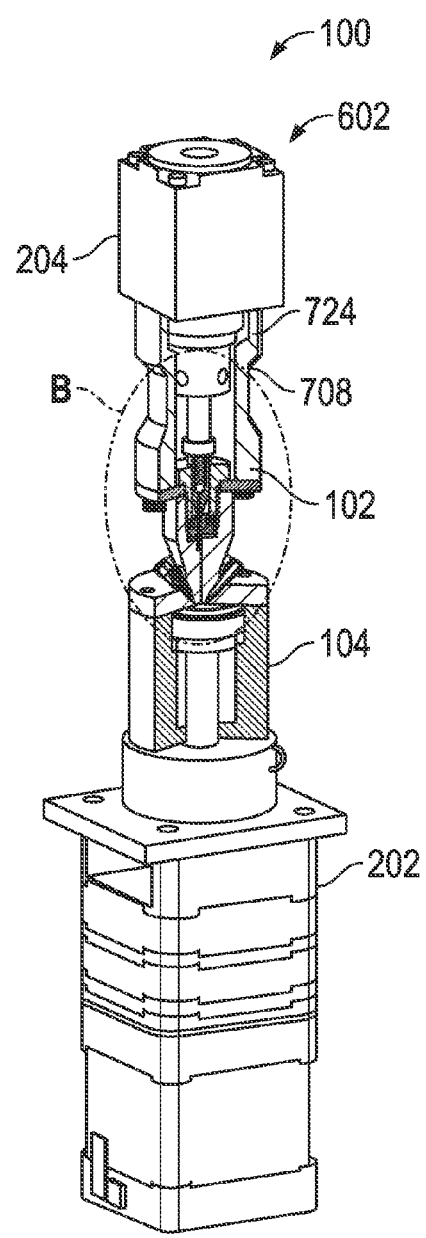
FIG. 11 is an illustration of isometric view of the embodiment of the present invention with the pump and valve actuators illustrating the second valve position illustrated in FIGS. 6 and 8 at the maximum position of the pump in the injection position.
Figure 12:
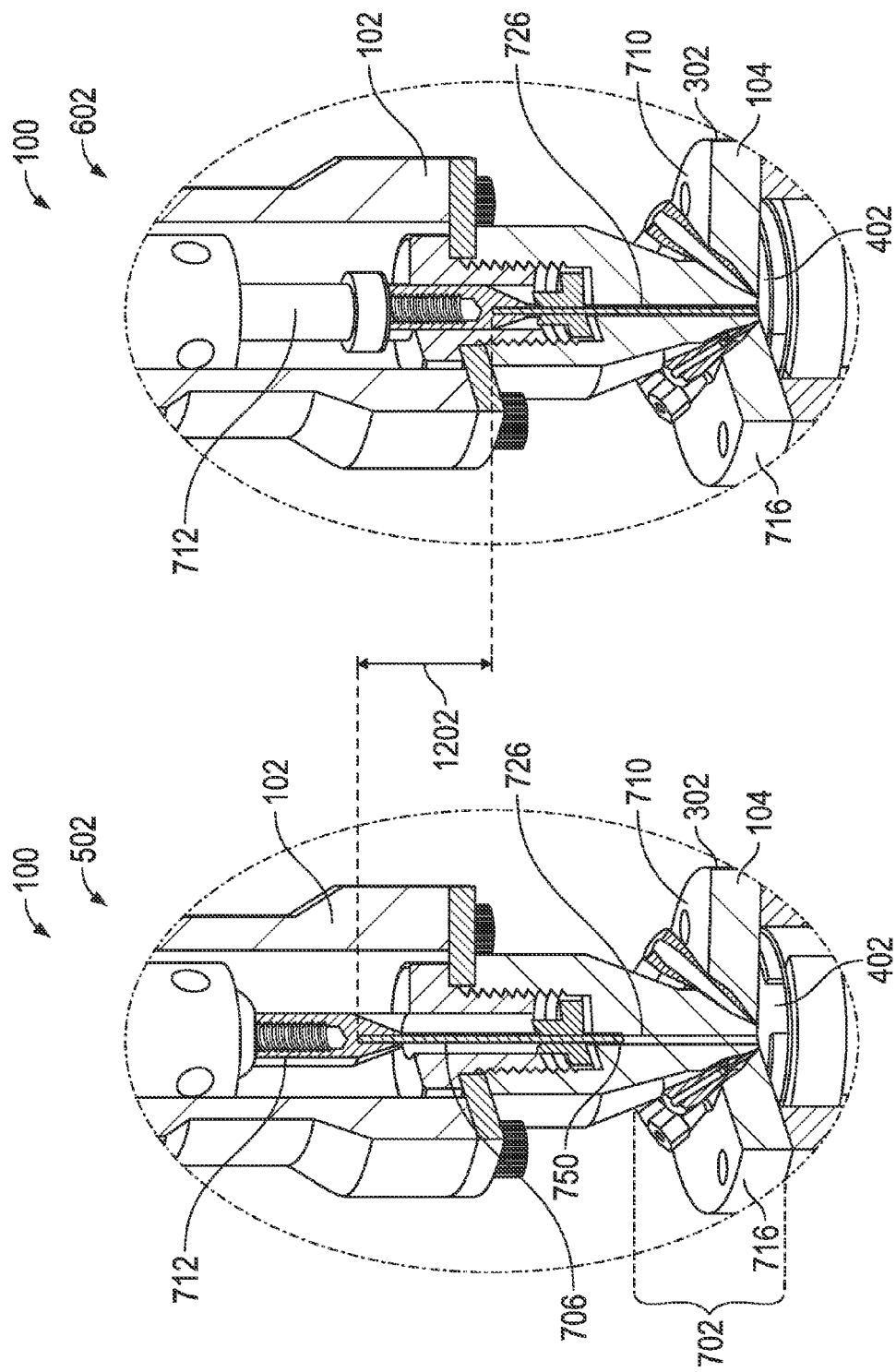
FIG. 12A is an enlargement of Section A of FIG. 10.
FIG. 12B is an enlargement of Section B of FIG. 11.
Figure 15:
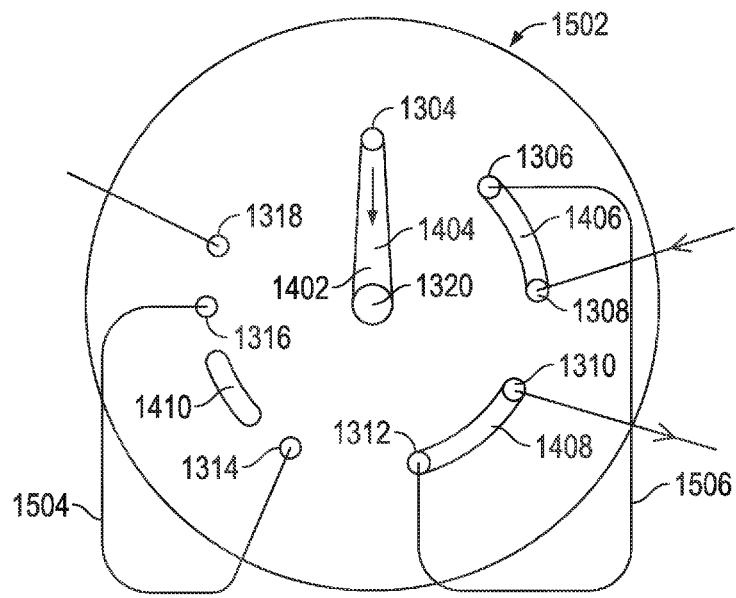
FIG. 15 is an illustration of the relative positions of the face of the stator and the face of the rotor of the alternative embodiment of the present invention in the load position.

In all embodiments, in the load position 502, 1502, 1710, 1928, the pump plunger 706 is retracted for filling the interior chamber 702 as illustrated in FIGS. 7, 10 and 12A. The plunger may have a diameter of 0.03 inches, or slightly smaller, or of 0.93 inches, or slightly larger, or may be between, such as 0.62 inches. The pump 708 thus includes a pump plunger 706, an interior chamber 702 defined by an elongate barrel 726 and the plunger 706. Referring to FIGS. 5, 7, 10, 12A and 15, the arrangement and nano-scale operation of integrated nano-scale pump and injection valve 100 is illustrated in at the maximum position of the pump 708 in the load position 502. The load position 502 of integrated nano-scale pump and injection valve 100, showing the positions of the stator 302 and the rotor 402 in the first embodiment, is depicted in FIG. 5. The load position 1502 of integrated nano-scale pump and injection valve 100, showing the positions of the stator 1302 and the rotor 1402 for the alternative embodiment is depicted in FIG. 15. As can be appreciated either the stator 302, 1302, 1712, 1932 or the rotor 402, 1402, 1702, 1902 will include a seal surface to contact the other. A cross-section illustration of the present invention along line Z-Z of FIG. 1 for the maximum position of the pump 708 in the load position 502, 1502, 1710, 1928 is illustrated in FIG. 7. An illustration of isometric view of the embodiment of the present invention with the valve actuator illustrating the first valve position is illustrated in FIG. 10. An enlargement of Section A of FIG. 10 is provided in FIG. 12A.

Figure 21:
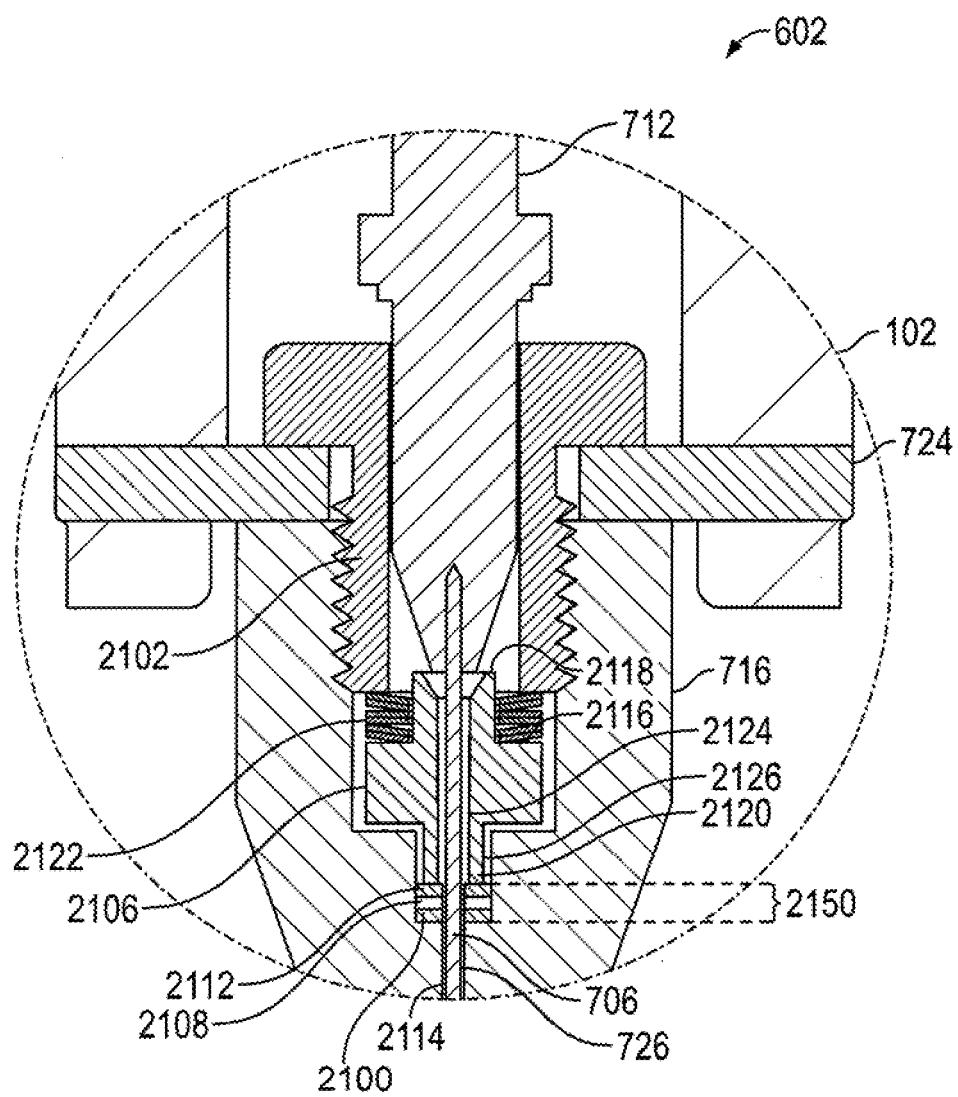
FIG. 21 is a close-up of the pump plunger driven forward for delivery for the maximum position of the pump in the injection position depicting a seal of the present disclosure.

Referring to FIG. 21, for operation at high pressure, such as above 10000 psi, it is essential that a strong seal 2150 be positioned about the plunger 706 within the barrel 726 of the integrated barrel-stator 716, at least a stroke-length 1202 above or beyond the first end 750 of the plunger 706 when in the maximum injection position so as to contact the plunger 706 and to form a seal thereabout. Positioning the seal 2150 less than a stroke-length 1202 from the first end 750 of the plunger 706 would cause the seal 2150 to fail when the plunger 706 was fully retracted to reach the maximum load position. While a single seal across the barrel 726, through which the plunger 706 would move, may be used, a composite seal is preferable. As depicted in FIG. 21, the seat 2150 about the plunger 706 within the barrel 726 may be formed of a compressed sequence of a first hard seal 2100, a flexible seal 2108, and a second hard seal 2112, placed under compression by a driving disk 2106 maintained within the integrated barrel-stator 716. The diameter of the barrel 726 of the integrated barrel-stator 716 is enlarged for that section more than a stroke-length 1202 above or beyond the first end 750 of the plunger 706 when in the maximum injection position to accept a first hard plastic seal 2100. The first hard plastic seal 2100 may be composed of a material such as polyether ether ketone (PEEK) or another material, and is sized to fit within the barrel 726 and about the plunger 706 without precluding movement of the plunger 706. Atop the first hard plastic seal 2100 is positioned a flexible seal 2108. The flexible seal 2108 is composed of a compressible sealing material, such as polytetrafluoroethylene (PTFE). The flexible seal 2108 is sized to fit within the barrel 726 and about the plunger 706 without precluding movement of the plunger 706. Atop the flexible seal 2108 is positioned a second hard plastic seal 2112, which may also may be composed of a material such as polyether ether ketone (PEEK) or another material, and is sized to fit within the barrel 726 and about the plunger 706 without precluding movement of the plunger 706. Compression of the flexible seal 2108 results in lateral expansion of the flexible seal 2108 and thereby causes the flexible seal 2108 to provide a seal against the plunger 706 which does not preclude movement of the plunger 706, between the first hard seal 2100 and the second hard seal 2112. This may be accomplished, by application of force against the second hard seal 2112 and a shoulder 2114 in the barrel 726 to maintain the position of the first hard seal 2100. The application of force against the second hard seal 2112 may be obtained by joining a threaded male sleeve or nut 2102, having a bore therethrough to freely accommodate the plunger 706 and piston 712 without interference, to the integrated barrel-stator 716, above or beyond the seal 2150, which threaded male sleeve 2102 would apply force to one or more springs 2122, particularly a Belleville spring also known as a coned disc spring, positioned within the integrated barrel-stator 716 above or adjacent the barrel 726, to force a driving disk 2106 to compress the second hard seal 2112. The threaded male sleeve 2102 is sized to a threaded female section of the integrated barrel-stator 716 above or adjacent the barrel 726. The driving disk 2106 includes a bore 2124 sized to permit the plunger 706 to pass therethrough without interference, a shoulder 2116 to permit the application of force against the driving disk 2106 from the springs 2122 smaller in diameter than the threaded male sleeve or nut 2102 so as not to contact the inner walls of the integrated barrel-stator 716, and a neck 2120 at its end 2126 proximate the barrel 726 sized to enter the barrel 726 without interference and having sufficient height to contact and apply force against the second hard seal 2112. As a result, the neck 2120 is driven against the second hard seal 2112, which is in turn driven into the flexible seal 2108 to compress it and form a seal about the plunger 706. The plunger 706 is therefore able to move through the seal 2150 without fluid seeping past, even as the flexible seal 2108 may become pliable during repeated movement of the plunger 706. Because only the seals 2112, 2108, 2100 laterally contact the plunger 706, and because the balance of the components, including the integrated barrel-stator 716, the threaded male nut or sleeve 2102, and the driving disk 2106, include sufficient clearance for the plunger 706 to move without interference, the plunger 706 can move within the barrel 726 and can operate to draw or eject fluid into the barrel 726 and through the stator 302, particularly at high pressure.

Thus, the seal 2150 includes a first hard plastic seal 2100, a flexible seal 2108, a second hard plastic seal 2112 and is compressed to seal about the plunger 706 by a driving disk 2106, a threaded male sleeve 2102, and one or more springs 2122. The first hard plastic seal 2100 is sized to fit within the barrel 726 and to fit about the plunger 706. The flexible seal 2108 is sized to fit within the barrel 726 and to fit about the plunger 706 adjacent the first hard plastic seal 2100. The second hard plastic seal 2112 is sized to fit within the barrel 726 and to fit about the plunger 706 adjacent the flexible seal 2108. The driving disk 2106 has a bore 2124 therethrough sized to fit about the plunger 706 without interference, a first end 2118 and a second end 2126. The driving disk 2106 is sized to freely fit within said integrated barrel-stator 716 adjacent the barrel 726, and includes a shoulder 2116 near the first end 2118, and a neck 2120 at the second end 2126, which neck 2120 is sized to fit within the barrel 726 and to contact the first hard plastic seal 2100. The threaded male sleeve 2102 has a bore therethrough sized to permit movement of the plunger 706 without interference and is sized to a threaded female section within the integrated barrel-stator 716 above, or adjacent, the barrel 726. The spring 2122 contacts the shoulder 2116 of the driving disk 2106 and an end of said threaded male sleeve 2102 and is compressed as the threaded male sleeve 2102 is driven into the integrated barrel stator 716.

Referring to FIG. 5, in the first embodiment, the valve 710 thus has a circular stator 302, formed integrally with the elongate barrel 726 to form integrated barrel-stator 716, and a circular rotor 402 where the two components cooperate to permit or preclude fluid communication among various parts of the valve 710. The stator 302 has an orifice 320 at its centerpoint, as well as a first stator port 304 for communication with a mobile phase supply, a second stator port 306 in communication with a fifth stator port 312, a third stator port 308 for communication with a sample reservoir, a fourth stator port 310 for outflow of sample waste, a sixth stator port 314 for communication with a chromatography column 504, a seventh stator port 316 for return from the chromatography column 504, and an eighth stator port 318 for outflow from the valve 710 such as to a detector. As both ends of the column 504 can be connected to the integrated nano-scale pump and injection valve 100 to maintain pressure during filling of the integrated nano-scale pump and injection valve 100 when the flow through the column 504 is stopped, if desired. This would eliminate a delay period for column re-pressurization. The rotor 402 therefore has a surface adjacent the stator 302 and three channels, or slots, 404, 406, 408 in its surface. The rotor 402 is rotable with respect to the stator 302 about the centerpoint between the load position 502 and the injection position 602. Rotation between the two positions may be 45 degrees about the centerpoint, or more or less, in the load position 502, components are isolated while the mobile phase is delivered to the internal chamber 702 of the pump 708, so that the first port 304 communicates with the orifice 320, and thereby to the internal chamber 702 of the pump 708, via the first channel 404, to provide filling, while all other ports are individually or paired in isolation, include the third port 308 and the fourth port 310, while communicating via the second channel 406 not otherwise communicating with any other components. The column 504 may therefore maintained at pressure and isolated while the interior chamber 702 of the pump 708 located in the pump section 102, as illustrated in FIG. 7, is filled by a mobile phase by drawing mobile phase through orifice 320, introduced via first channel 404 which is connected to port 304. For initial charging of the column 504, the operator can run the mobile phase through the second channel 406, the sample channel, switching between the load position 502 and the injection position 602 to fill the column 504 and to ensure no bubbles are present in the system. In the load position 502, the port 318, which may be connected to a detector, is likewise isolated. Referring to FIGS. 3 and 4, and more particularly to FIG. 5, in this load position 502, with reference to stator 302 and rotor 402, ports 306 and 312 are in communication to form a loop 506, to provide an internal sample, but are otherwise isolated. This loop 506 may be of 5.08 cm×75 or 150 μm inner diameter stainless steel tubing to carry the mobile phase to the column during injection (dispensing). A sample is introduced to and flows through the integrated nano-scale pump and injection valve 100 at port 308, the sample inlet port, which is connected via second channel 406 to port 310, the waste outlet port. As can be appreciated each port is associated with a connector 206 on the intersection of the pump section 102 and the valve section 104. During the introduction of the sample, second channel 406 therefore contains the sample to be tested. Thus, in this load position 502, a sample, which may originate from an external reservoir, may be flowed through an internal passage. In the injection position 602, mobile phase is delivered from the pump 708 and directed through the valve 710 to the column 504 and potentially to a downstream detector by connecting the orifice 320, which is in communication with the pump 708, and the second port 306 via the first channel 404, by connecting the fifth port 312 and the sixth port 314 via the second channel 406, which thereby provides a complete flow path to the chromatography column 504, and by connecting the seventh port 316, which is in communication with the outflow of the column 504, with the eighth port 318 via the third channel 408 so that the sample separated by the column 504 may be processed by a detector. As can be appreciated, in a secondary embodiment, the seventh port 316, the eighth port 318 and the third channel 408 could be omitted and the outflow from the column 504 provided directly to a detector or other equipment.

Due to the volumes involved, refilling of the integrated nano-scale pump and injection valve 100 may be accomplished is less than 2 minutes. Since typical flow rates used in capillary columns (100-150 μm i.d.) range from 100 to 500 nL/min, an isocratic separation can be easily completed without the need to refill the integrated nano-scale pump and injection valve 100.

In the alternative embodiment, such as depicted in FIGS. 13, 14, 15, and 16, the valve 710 has a circular stator 302, again formed integrally with the elongate barrel 726, and a circular rotor 402 where the two components cooperate to permit or preclude fluid communication among various parts of the valve. As with the stator of the first embodiment, the stator 1302 has an orifice 1320 at its centerpoint with the pump 708 in communication with the valve 710 at the orifice 1320, a first stator port 1304 for communication with a mobile phase supply, a second stator port 1306 in communication with a fifth stator port 1312 via a loop 1506, a third stator port 1308 for communication with a sample reservoir, a fourth stator port 1310 for outflow, a sixth stator port 1314 for communication with a chromatography column 1504, a seventh stator port 1316 for return from the chromatography column 1504, and an eighth stator port 1318 for outflow from the valve 710 such as to a detector. The rotor in the alternative embodiment includes the four channels 1404, 1406, 1408, 1410 in its surface, in the alternative embodiment, the load position 1502 is defined by the first port 1304 and the orifice 1320 communicating with the first channel 1404, by the second port 1306 and the third port 1308 communicating with the second channel 1406, and the fourth port 1310 and the fifth port 1312 communicating with the third channel 1408. In the alternative embodiment, as illustrated in FIG. 15, the column 504 is attached to port 1314, column inflow, and port 1316, column outflow, which are otherwise isolated. The column 1504 is therefore maintained at pressure and isolated while the interior chamber 702 of the pump 708 located in the pump section 102, as illustrated in FIG. 7, is filled by a mobile phase by drawing mobile phase through orifice 1320, introduced via the first channel 1404, the fill/dispense channel, which is connected to port 1304. In the load position 502, the port 318, which may be connected to a detector, is likewise isolated. Referring to FIGS. 13 and 14, and more particularly to FIG. 15, in this load position 502, with reference to stator 1302 and rotor 1402, ports 1306 and 1312 are in communication to form a loop 1506 but are otherwise isolated. A sample is introduced to and flows through the integrated nano-scale pump and injection valve 100 at port 1308, the sample inlet port, which is connected via second channel 1406 to port 1306 and then, via a loop 1506 to port 1312, which is then in communication with port 1310 via third channel 1408, the waste outlet port. As can be appreciated each port is associated with a connector 206. During the introduction of the sample, the sample to be tested is contained with the channel 1406 and the loop 506, providing for an increased sample size. Thus, in this load position 502, a sample, which may originate from an external reservoir, may be flowed through an internal passage. In the alternative embodiment, the injection position 1602 is defined by the orifice 1320 and the second port 1306 communicating with the first channel 1404, by the fifth port 1312 and the sixth port 1314 communicating with the third channel 1408, and by the seventh port 1316 and the eighth port 1318 communicating with the fourth channel 1410.

In the first embodiment, the second channel 406 defines the nano-scale sample size while the interior chamber 702 contains the volume from which mobile phase is pumped. In the alternative embodiment, the third channel 1408 and the loop 1506 define the nano-scale sample size.

Figure 6:
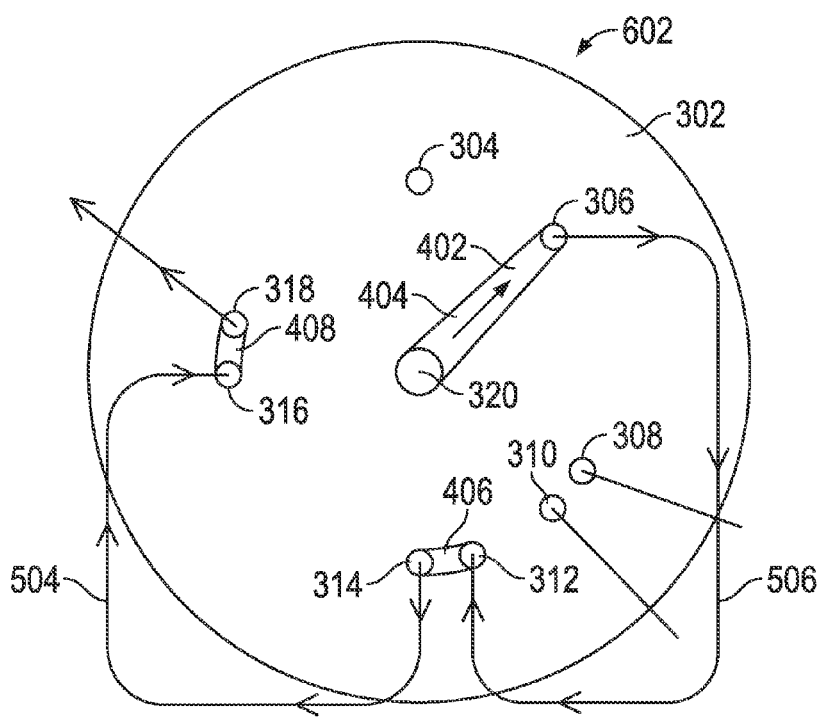
FIG. 6 is an illustration of the relative positions of the face of the stator and the face of the rotor of the first embodiment of the present invention in the injection position.
Figure 8:
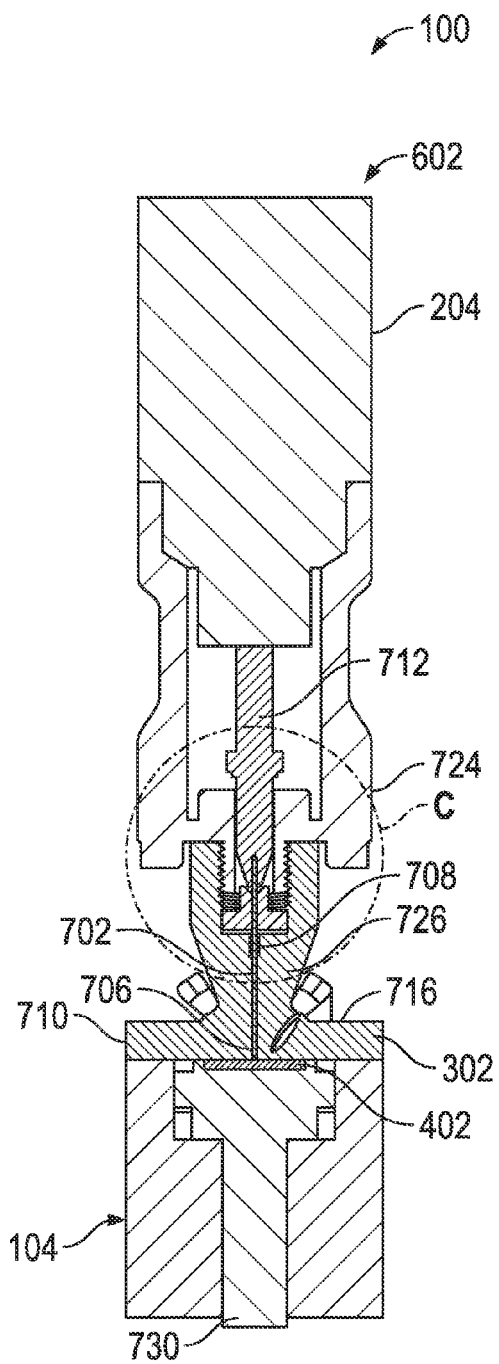
FIG. 8 is a cross-section illustration of the present invention along line Z-Z of FIG. 1 for the maximum position of the pump in the injection position in connection with a linear actuator.
Figure 9:
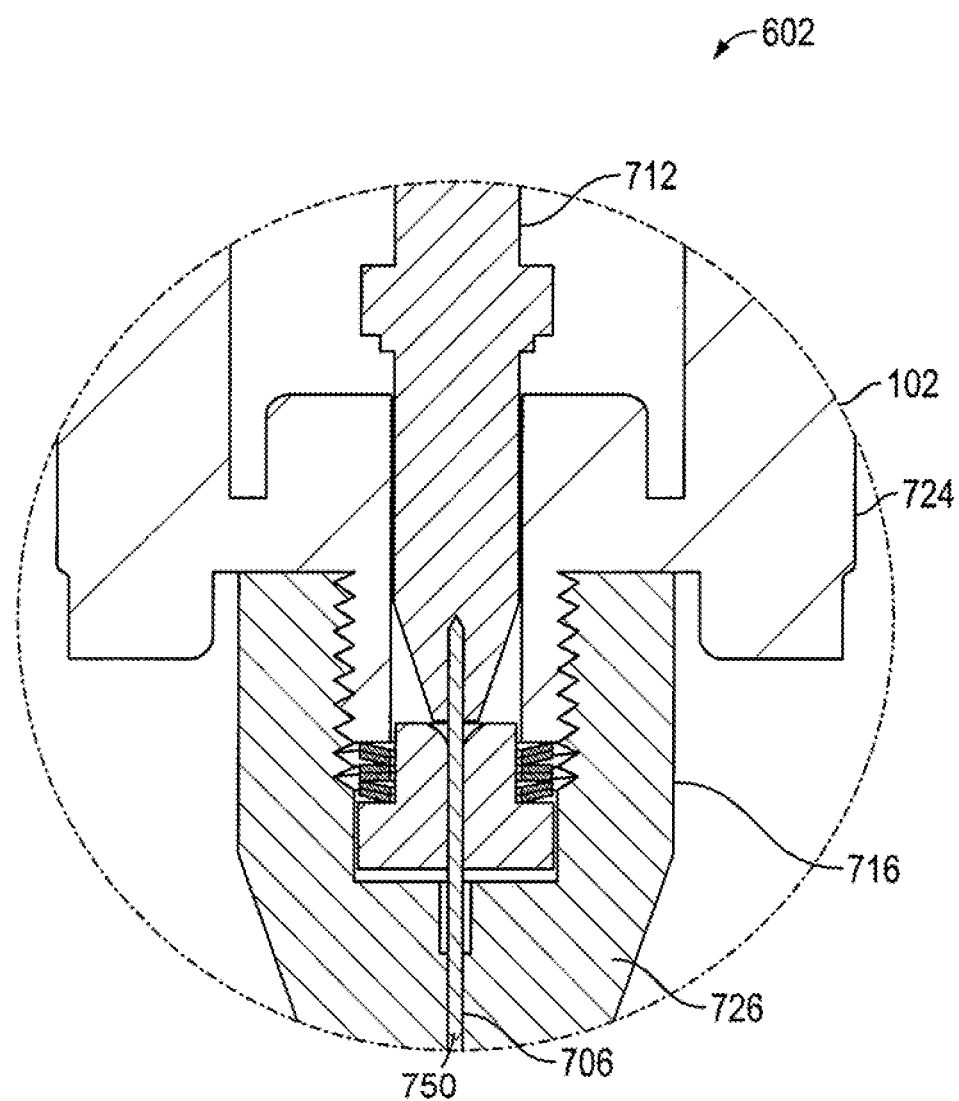
FIG. 9 is a close-up of the pump plunger driven forward for delivery for the maximum position of the pump in the injection position.

Referring to FIGS. 6, 8, 9, 11, and 12B, the nano-scale operation of the pump section 102 is illustrated in the injection position 602 for the first embodiment. The injection position 602 of the nano-scale operation of the pump section 102, showing the positions of the stator 302 and the rotor 402, is depicted in FIG. 6. As illustrated in FIG. 6, the rotor is rotated 45 degrees, preferably by a mechanical valve actuator 202 coupled to act in concert with the action of the linear pump actuator 204, generating a new flow path within the valve 710. The relative position between the stator 302 and the rotor 402 may be set to provide for a greater or lesser rotation. Referring to FIG. 6, the first channel 404, the fill/dispense channel, connects the internal pump 708, via orifice 320, to the loop 506 at port 312. The loop 506 now connects to second channel 406 containing the sample. Ports 308 and 310 are now isolated, preventing further inflow of any sample. Similarly, port 304 is isolated, preventing further inflow of mobile phase. As second channel 406 containing the sample now connects to the inlet of the column 504 via port 314 and as channel 408 now connects the outlet of the column 504, at port 316, to the port 318, the outlet to the detector, a complete flow path is established and the mobile phase pushes the sample through the column 504 and to any connected detector. This is accomplished by the pump plunger 706 being driven toward the valve 710 as illustrated in FIGS. 8, 10 and 12B, displacing fluid from the interior chamber 702 into the valve 710. Thus, the pump 708 delivers fluid through the sample passage of second channel 406 into the column 504. When the drive shaft 730 of the valve 710 is rotated by a valve actuator 202, the pump 708 is started, which results in the pump 708 starting the moment the endpoint is reached and thus avoids the column bed becoming unstable. As can be appreciated, upon completion of the analysis, the integrated nano-scale pump and injection valve 100 is returned to the load position 502, the filling position.

Figure 16:
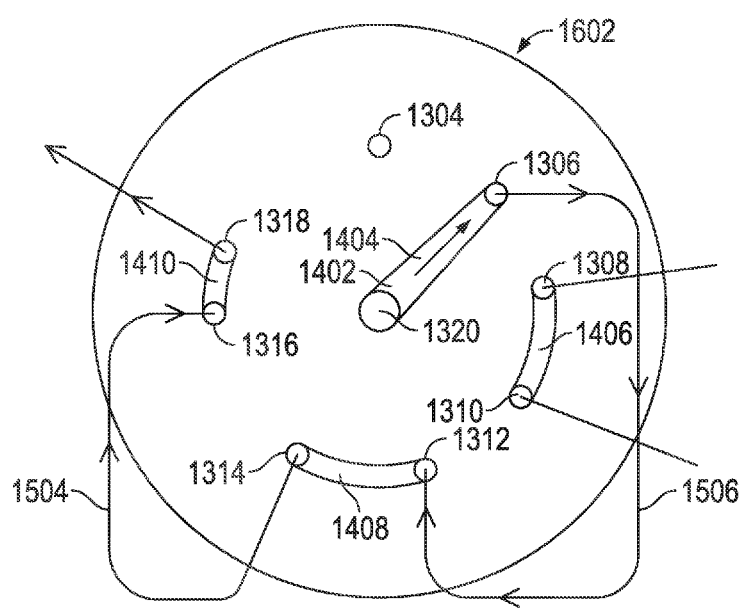
FIG. 16 is an illustration of the relative positions of the face of the rotor and the face of the rotor of the alternative embodiment of the present invention in the injection position.

Referring to FIGS. 8, 9, 11, 12B, and 16, the nano-scale operation of the pump section 102 is illustrated in the injection position 1602 for the second embodiment. The injection position 1602 of the nano-scale operation of the pump section 102, showing the positions of the stator 1302 and the rotor 1402, is depicted in FIG. 16. As illustrated in FIG. 16, the rotor is rotated 45 degrees, preferably by a mechanical valve actuator 202 coupled to act in concert with the action of the linear pump actuator 204, generating a new flow path within the valve 710. The relative position between the stator 1302 and the rotor 1402 may be set to provide for a greater or lesser rotation. Referring to FIG. 16, first channel 1404, the fill/dispense channel, connects the internal pump 708, via orifice 1320, to the loop 1506 at port 1312. The loop 1506, containing some sample, connected to third channel 1408 also containing some sample, now connects to the inlet of the column 1504 via port 1314 and as third channel 1408 now connects the outlet of the column 1504, at port 1316, to the port 1318, the outlet to the detector, a complete flow path is established and the mobile phase pushes the sample through the column 1504 and to any connected detector. This is accomplished by the pump plunger 706 being driven toward the valve 710 as illustrated in FIGS. 8, 10 and 12B, displacing fluid from the interior chamber 702 into the valve 710. Thus, the pump 708 delivers fluid into the column 504. Ports 1308 and 1310 are isolated, preventing further inflow of any sample. Similarly, port 1304 is isolated, preventing further inflow of mobile phase. When the drive shaft 730 of the valve 710 is rotated by a valve actuator 202, the pump 708 is started, which results in the pump 708 starting the moment the endpoint is reached and thus avoids the column bed becoming unstable. As can be appreciated, upon completion of the analysis, the integrated nano-scale pump and injection valve 100 is returned to the load position 502, the filling position.

Figure 17:
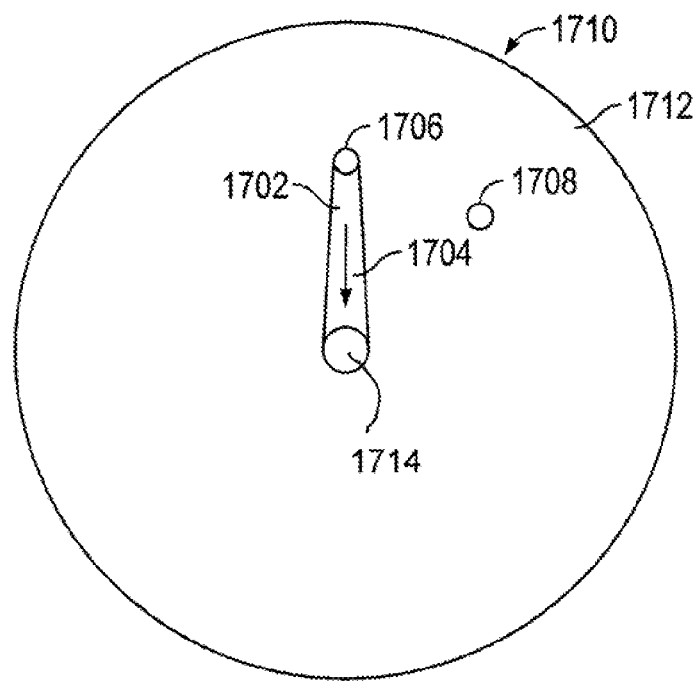
FIG. 17 is an illustration of the relative positions of the face of the stator and the face of the rotor of the further alternative embodiment of the present invention in the load position.
Figure 18:
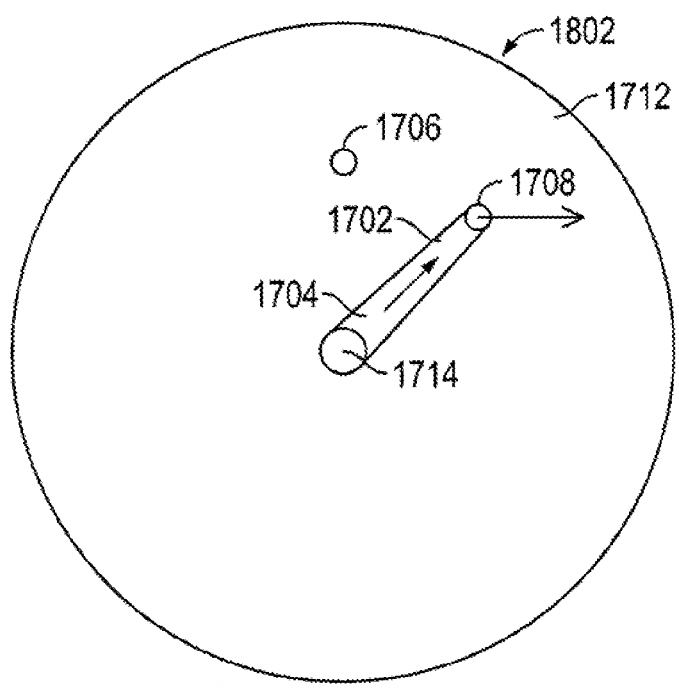
FIG. 18 is an illustration of the relative positions of the face of the rotor and the face of the rotor of the further alternative embodiment of the present invention in the injection position.

Referring to FIGS. 17 and 18, the present disclosure may alternatively be used as a pump without regard to the equipment connected thereto. In the further alternative embodiment, the rotor 1702 has a channel 1704 and the stator 1712 has a first stator port 1706 for communication with a mobile phase supply, an orifice 1714 in communication with the elongate barrel 726 and a second stator port 1708 for communication with an external device. In the further alternative embodiment, the load position 1710, as illustrated in FIG. 17, is defined by the first port 1706 and the orifice 1714 communicating with the channel 1704 and the injection position 1802 is defined by the orifice 1714 and the second port 1708 communicating with the channel 1704. As can be appreciated, any number of additional ports may be positioned on the stator 1712 to permit the pump to draw fluid through the first port 1706 to be pumped to any one of a plurality of ports, providing a multiple position valve.

Figure 19:
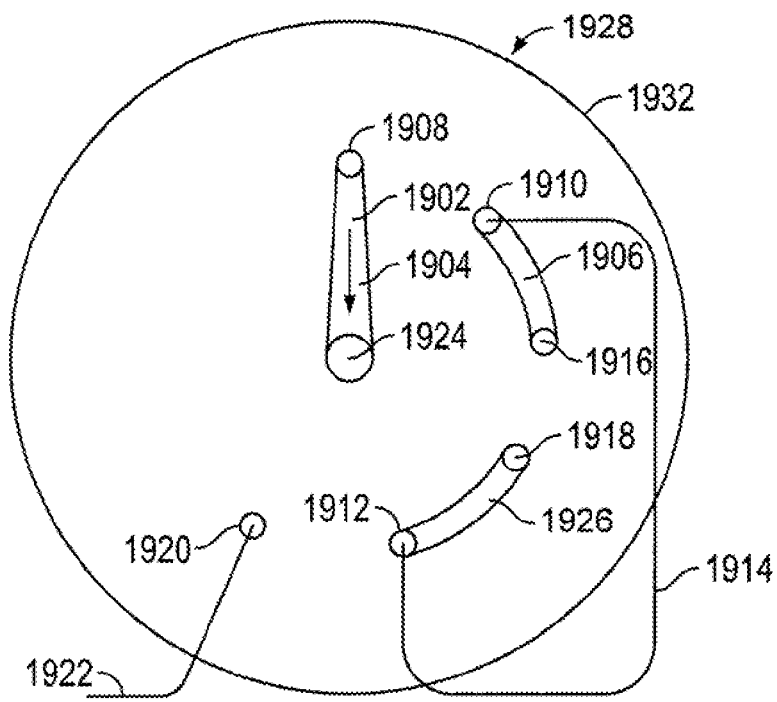
FIG. 19 is an illustration of the relative positions of the face of the stator and the face of the rotor of the additional alternative embodiment of the present invention in the load position.
Figure 20:
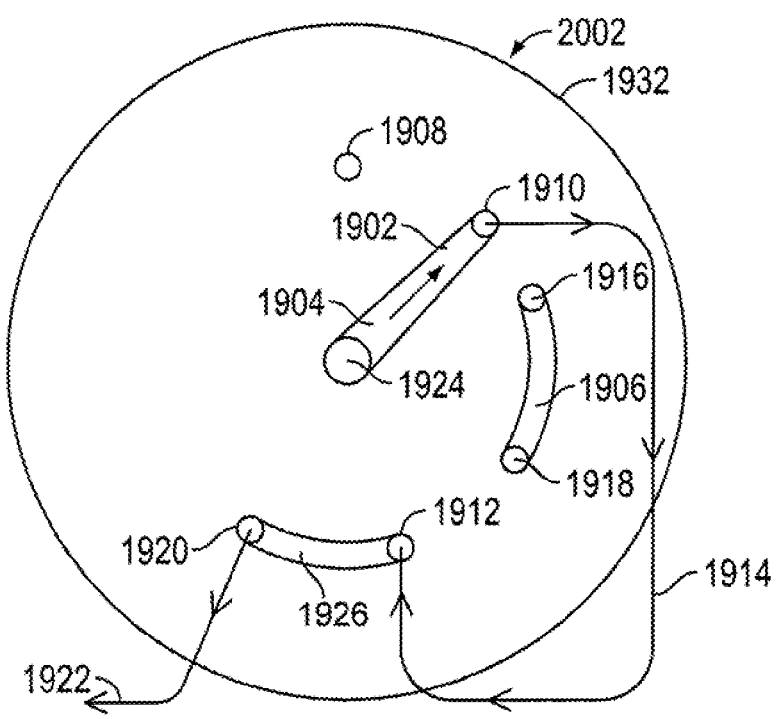
FIG. 20 is an illustration of the relative positions of the face of the rotor and the face of the rotor of the additional alternative embodiment of the present invention in the injection position.

Referring to FIGS. 19 and 20, the present disclosure may be used to push a sample through a column, wherein the output of the column is provided to other equipment rather than through the valve. In the additional alternative embodiment, the rotor 1902 has a first channel 1904, a second channel 1906, and a third channel 1926, and the stator 1932 has the orifice 1924 in communication with the elongate barrel 726, a first stator port 1908 for communication with a mobile phase supply, a second stator port 1910 in communication with a fifth stator port 1912 via an external loop 1914, a third stator port 1916 for communication with a sample reservoir, a fourth stator port 1918 for sample outflow, and a sixth stator port 1920 for communication with a chromatography column 1922. In the additional alternative embodiment, the load position 1928 is defined by the first port 1908 and the orifice 1924 communicating with a first channel 1904, by the second port 1910 and the third port 1916 communicating with the second channel 1906, and the fourth port 1918 and the fifth port 1912 communicating with the third channel 1926. In the alternative embodiment, the injection position 2002 is defined by the orifice 1924 and the second port 1910 communicating with the first channel 1904, and by the fifth port 1912 and the sixth port 1920 communicating with the third channel 1926, which is connected to a column 1922 connected to the sixth port 1920.

Figure 22:
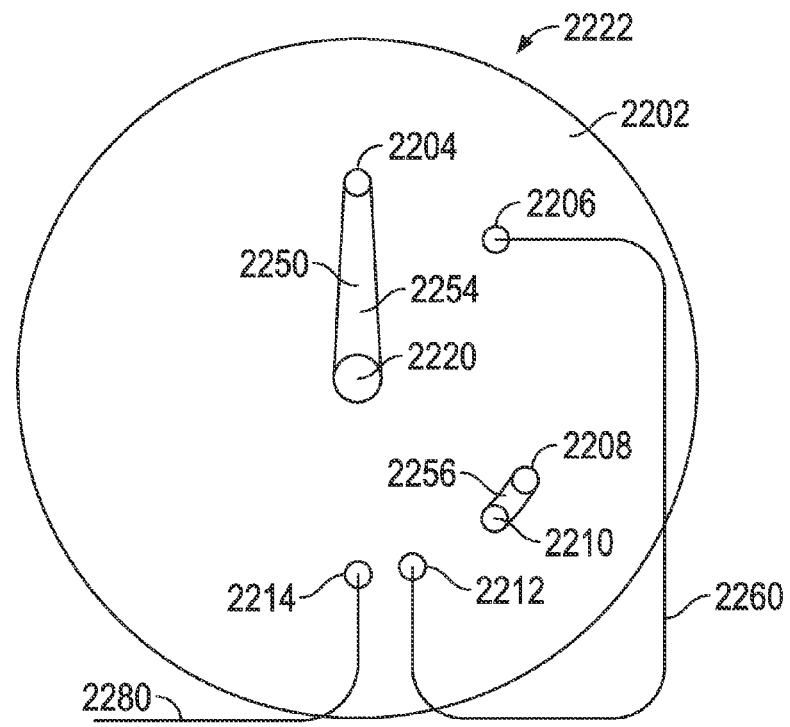
FIG. 22 is an illustration of the relative positions of the face of the stator and the face of the rotor of the additional alternative, embodiment of the present invention in the load position.
Figure 23:
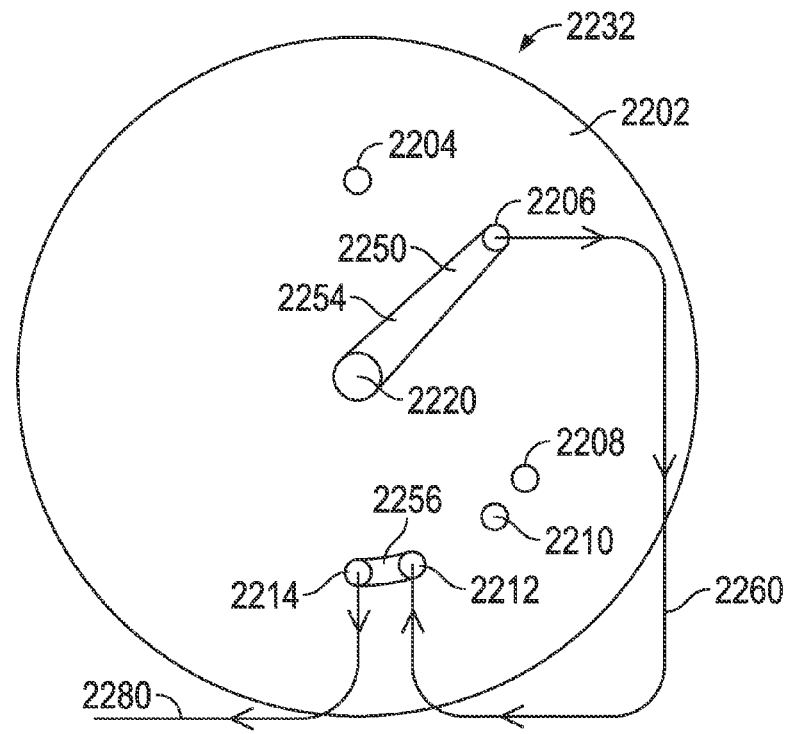
FIG. 23 is an illustration of the relative positions of the face of the rotor and the face of the rotor of the additional alternative embodiment of the present invention in the injection position.

Referring to FIGS. 22 and 23, the present disclosure may be used to push an internal sample through a column, wherein the output of the column is provided to other equipment rather than through the valve, incorporating the structure and flow paths of the first embodiment depicted in FIGS. 3-6 excerpt for the third channel 408, and the seventh port 316 and the eighth port 318, which are omitted. FIG. 22 is an illustration of the relative positions of the face of the stator and the face of the rotor of the additional alternative embodiment of the present invention in the load position. FIG. 23 is an illustration of the relative positions of the face of the rotor and the face of the rotor of the additional alternative embodiment of the present invention in the injection position. Referring to FIG. 22, the valve 710 has a circular stator 2202, formed integrally with the elongate barrel 726 to form integrated barrel-stator 716, and a circular rotor 2250 where the two components cooperate to permit or preclude fluid communication an various parts of the valve 710. The stator 2202 has an orifice 2220 at its centerpoint, as well as a first stator port 2204 for communication with a mobile phase supply, a second stator port 2206 in communication with a fifth stator port 2212 via a loop 2260, a third stator port 2208 for communication with a sample reservoir, a fourth stator port 2210 for outflow of sample waste, and a sixth stator port 2214 for communication with a chromatography column 2280. The rotor 2250 therefore has a surface adjacent the stator 2202 and two channels, or slots, 2254, 2256 in its surface. The rotor 2250 is rotable with respect to the stator 2202 about the centerpoint between the load position 2222 and the injection position 2232. The injection position 2232 of the nano-scale operation of the pump section 102, showing the positions of the stator 2202 and the rotor 2250, is depicted in FIG. 23. The first channel 2254, the fill/dispense channel, connects the internal pump 708, via orifice 2220, to the loop 2260 at port 2212. The loop 2260 now connects to second channel 2256 containing the sample. Ports 2208 and 2210 are now isolated, preventing further inflow of any sample. Similarly, port 2204 is isolated, preventing further inflow of mobile phase. As second channel 2256 containing the sample now connects to the inlet of the column 2280 via port 2214, providing a complete flow path so the mobile phase pushes the sample through the column 2280 and to any connected detector.

The stroke of the pump section 102, as illustrated in general in FIGS. 7 and 8, is particularly illustrated in FIGS. 12A and 12B, wherein the stroke 1202 of the pump section 102 is illustrated between the maximum load position 502, 1502, 1710, 1928 and the maximum injection position 602, 1602, 1802, 2002. The stroke 1202 may be 0.25 inches, or slightly smaller, or 0.75 inches, or slightly larger, or may be between, such as at 0.50 inches. As can be appreciated, the stroke 1202 and the diameter of the barrel 726 determine the volume of fluid transmitted during each load and injection cycle, which, by virtue of their values, are measured in microliters. Operation of the invention and the associated low flow rates are made possible by use of the integration of the pump section 102 and the valve section 104, unlike conventional products.

Referring to FIGS. 7, 8, 9, 10, 11, 12A and 12B, operation of the integrated nano-scale pump and injection valve 100 is provided by the body 724, the linear pump actuator 204, and the integrated barrel-stator 716. The linear pump actuator 204 includes a plunger-driving piston 712 connected to the plunger 706. A plunger 706, at least equal in length to the stroke 1202 and nearly-equivalent to the diameter of the interior chamber 702, is attached to the end of the plunger-driving piston 712. In the load position 502, 1502, 1710, 1928, the plunger 706 is at its maximum retraction within the elongate barrel 726 and defines the maximum volume which may be moved during the stroke 1202. In the injection position 602, 1602, 1802, 2002, the plunger 706 is at its maximum displacement into the elongate barrel 726. The volume displaced during the stroke 1202 between the maximum position associated with the loading 502, 1502, 1710, 1928 and the maximum position associated with the injection 602, 1602, 1802, 2002 is equal to the volume of the plunger 706 introduced into the elongate barrel 726. The position of the plunger 706 in the barrel 726 and its extent during the stroke be determined with mechanical systems such as optical encoders, or others known in the art, and the maximum extent may be defined and operation limited by mechanical stops or limit switches.

Thus, the integral nano-scale pump and injection valve 100 includes a body having a pump section 102 and a valve section 104 where the body has a pump 708 in the pump section 102 and a valve 710 in the valve section 104. The pump 708 functions linearly by using an elongate barrel 726 and a plunger 706. As the barrel provides an internal chamber in which the plunger 706 moves, drawing or ejecting fluid from one end while the plunger 706 is moved from the opposing end, the elongate barrel 726 is characterized by an open proximal end, an open distal end, a length, and a sidewall, which define the interior chamber 702. As detailed, the internal chamber 702 is adapted to receive a supply of mobile phase, and provides operation in connection with the plunger 706 by having an inner diameter sized to the plunger, an outer diameter sized to fit within the pump section and a wall thickness therebetween to provide sufficient strength. The plunger 706, which has a substantially uniform cross-section, is slidably disposed within the interior chamber 702 and is sized to ensure effective operation during the load position 502, 1502, 1710, 1928 and the injection position 602, 1602, 1802, 2002.

The present invention provides an integral nano-scale pump and injection valve 100 for high performance liquid chromatography which includes an integrated barrel-stator 716, which has an elongate barrel 726 at a first end and a stator 302, 1302, 1712, 1932 at a second end, a plunger 706 slidably disposed within an interior chamber 702 of the barrel 726 of substantially uniform cross-section, and a rotor 402, wherein the pump 708 and valve 710 are switchable between a load position 502, 1502, 1710, 1928 and a injection position 602, 1602, 1802, 2002. The circular rotor 402 has a surface adjacent the stator 302 and has a plurality of channels 404, 406, 408, 1404, 1406, 1408, 1410 in its surface and is rotatable with respect to the stator 302, 1302 about a centerpoint between the load position 502, 1502, 1710, 1928 and the injection position 602, 1602, 1802, 2002. The elongate barrel 726 portion of the integrated barrel-stator 716 includes an open proximal end, an open distal end, a length, and a sidewall defining the interior chamber 702 adapted to receive a supply of fluid and which has an inner diameter, an outer diameter, and a wall thickness. The circular stator 302 has an orifice 320 at its centerpoint and a first side and a second side such that the elongate barrel open distal end is aligned with the second side of the stator 302 at the centerpoint and the interior chamber 702 includes the orifice 320. The pump 708 is therefore in communication with the valve 710 at the orifice 320.

The nano-scale operation of the integrated nano-scale pump and injection valve 100 is made possible by integration of parts may be further augmented by sufficient and operable 360 zero-dead volumemicrometer fittings, and by material selection. Diamond-coated surfaces may be utilized where beneficial. The plunger 706 may be constructed of a work hardened super alloy, such as MP35N, a nickel-chromium-molybdenum-cobalt alloy providing ultra-high strength, toughness, ductility and high corrosion resistance—particularly from contact with hydrogen sulfide, chlorine solutions and mineral acids (nitric, hydrochloric, and sulfuric). Moveover, the nano-scale operation of the integrated nano-scale pump and injection valve 100 permits portability, such as being battery-operated, while being light weight, having low mobile phase consumption and generating low waste. Additionally, this system, designed particularly for capillary column use, does not employ a splitter, provides a substantial in operation. The integrated nano-scale pump and injection valve 100 can generate up to 110.32 MPa (16,000 psi) pressure, with a pump volume capacity of 24 µL, and a sample volume as low as 10 nL, or higher, such as 60 nL, can be injected As a result of the structures provided herein, the maximum and minimum dispensing volumetric flow rates of the integrated nano-scale pump and injection valve 100 are 74.2 µL/min and 60 nL/min, respectively. This may further be accomplished by providing the loop 506 of 5.08 cm×75 or 150 µm inner diameter stainless steel tubing to carry the mobile phase to the column during injection (dispensing).

The terms and expressions which have been employed in the foregoing specification are used therein as terms of description and not of limitation, and there is no intention, in the use of such terms and expressions, of excluding equivalents of the features shown and described or portions thereof.

We claim:

1. An integral nano-scale pump and injection valve for high performance liquid chromatography comprising:

an integrated barrel-stator, said integrated barrel-stator having an elongate barrel and a stator, said integrated barrel-stator integrally-formed of a single piece of monolithic material, said elongate barrel having a first open end at a first end of said integrated barrel-stator a second open end at a second end of said integrated barrel-stator and a sidewall defining an interior chamber adapted to receive a supply of fluid, said stator being circular, said stator having a first side, said elongate barrel second end terminating at a centerpoint of said stator at said stator first side and providing an orifice, said stator first side being coplanar with said second end of said integrated barrel-stator, said stator having a first stator port for communication with a mobile phase supply, said stator in communication with a rotor at said orifice, said stator at said second end of said integrated barrel-stator, a longitudinal plunger slidably extending into said interior chamber at said first end of said integrated barrel-stator, said plunger being of substantially uniform cross-section; and said rotor being circular, said rotor having a surface adjacent said stator, said rotor having a first channel in said surface, said rotor rotable with respect to said stator about said centerpoint of said stator between a load position and an injection position, said load position defined by said first stator port and said orifice communicating with said first channel, and said injection position defined by said orifice and a second stator port communicating with said first channel.

2. The integral nano-scale pump and injection valve of claim 1 further comprising:

a first hard plastic seal about said plunger sized to fit within said elongate barrel and to fit about said plunger;

a flexible seal about plunger sized to fit within said barrel and to fit about said plunger adjacent said first hard plastic seal;

a second hard plastic seal about plunger sized to fit within said elongate barrel and to fit about said plunger adjacent said flexible seal;

a driving disk having a bore therethrough sized to fit about said plunger without interference, said driving disk having a driving disk first end and a driving disk second end, said driving disk sized to freely fit within said integrated barrel-stator barrel adjacent said elongate barrel, said driving disk having a shoulder near said driving disk first end and a neck at said driving disk second end, said neck sized to fit within said barrel and to contact said first hard plastic seal, a threaded male sleeve having a bore therethrough sized to permit movement of said plunger without interference, said threaded male sleeve sized to a threaded female section within said integrated barrel-stator adjacent said elongate barrel; and a spring contacting said shoulder of said driving disk and an end of said threaded male sleeve.

3. The integral nano-scale pump and injection valve of claim 2, further comprising a pump actuator associated with a plunger-driving piston attached to said plunger.

4. The integral nano-scale pump and injection valve of claim 3, further comprising a valve actuator associated with a driveshaft attached to said rotor.

5. The integral nano-scale pump and injector injection valve of claim 2 further comprising:
said stator having the second stator port in communication with a fifth stator port, a third stator port for communication with a sample reservoir, a fourth stator port for outflow, a sixth stator port for communication with a chromatography column, a seventh stator port for return from said chromatography column, and an eighth stator port for outflow from said integral nano-scales pump and injection valve,
said rotor having a second channel in said surface, and a third channel in said surface,
said load position further defined by said third stator port and said fourth stator port communicating with said second channel; and
said injection position further defined by said fifth stator port and said sixth stator port communicating with said second channel, and by said seventh stator port and said eighth stator port communicating with said third channel.

6. The integral nano-scale pump and injection valve of claim 5, further comprising a pump actuator associated with a plunger-driving piston attached to said plunger.

7. The integral nano-scale pump and injection valve of claim 6, further comprising a valve actuator associated with a driveshaft attached to said rotor.

8. The integral nano-scale pump and injection valve of claim 2 further comprising:
said stator having the second stator port in communication with a fifth stator port via loop, a third stator port for communication with a sample reservoir, a fourth stator port for outflow, a sixth stator port for communication with a chromatography column, a seventh stator port for return from said chromatography column, and an eighth stator port for outflow from said integral nano-scales pump and injection valve,
said rotor having a second channel in said surface, a third channel in said surface, and a fourth channel in said surface;
said load position further defined by said second stator port and said third stator port communicating with said second channel, and said fourth stator port and said fifth stator port communicating with said third channel; and
said injection position further defined by said fifth stator port and said sixth stator port communicating with said third channel, and by said seventh stator port and said eighth stator port communicating with said fourth channel.

9. The integral nano-scale pump and injection valve of claim 8, further comprising a pump actuator associated with a plunger-driving piston attached to said plunger.

10. The integral nano-scale pump and injection valve of claim 9, further comprising a valve actuator associated with a driveshaft attached to said rotor.

11. The integral nano-scale pump and injection valve of claim 2 further comprising:
said stator having the second stator port in communication with a fifth stator port via loop, a third stator port for communication with a sample reservoir, a fourth stator port for outflow, a sixth stator port for communication with a chromatography column, said rotor having a second channel in said surface, said rotor rotable with respect to said stator about said centerpoint of said stator between a load position and an injection position,
said load position further defined by said fourth stator port and said third stator port communicating with said second channel; and
said injection position further defined by said fifth stator port and said sixth stator port communicating with said second channel.

12. The integral nano-scale pump and injection valve of claim 11, further a pump actuator associated with a plunger-driving piston attached to said plunger.

13. The integral nano-scale pump and injection valve of claim 12, further comprising a valve actuator associated with said rotor.

14. The integral nano-scale pump and injection valve of claim 2 further comprising:
said stator having the second stator port in communication with a fifth stator port, a third stator port for communication with a sample reservoir, a fourth stator port for outflow, and a sixth stator port for communication with a chromatography column;
said rotor having a second channel in said surface;
said load position further defined by said third stator port and said fourth stator port communicating with said second channel; and
said injection position further defined by said fifth stator port and said sixth stator port communicating with said second channel.

15. The integral nano-scale pump and injection valve of claim 14, further comprising a pump actuator associated with a plunger-driving piston attached to said plunger.

16. The integral nano-scale pump and injection valve of claim 15, further comprising a valve actuator associated with a driveshaft attached to said rotor.

17. An integral nano-scale pump and injection valve for high performance liquid chromatography comprising:
an integrated barrel-stator, said integrated barrel-stator having an elongate barrel and a stator, said integrated barrel-stator integrally-formed of a single piece of monolithic material,
said elongate barrel having a first open end at a first end of said integrated barrel-stator and a second open end at a second end of said integrated barrel-stator and a sidewall defining an interior chamber adapted to receive a supply of fluid,
said stator being circular, said stator having a first side, said elongate barrel second end terminating at a centerpoint of said stator at said stator first side at an orifice, said stator first side being coplanar with said second end of said integrated barrel-stator, said stator at said second end of said integrated barrel-stator,
said elongate barrel in communication with a rotor at said orifice, said stator having a first stator port for communication with a mobile phase supply,
a longitudinal plunger slidably extending into said interior chamber at said first end of said integrated barrel-stator, said plunger being of substantially uniform cross-section; and
said rotor being circular, said rotor having a surface adjacent said stator, said rotor having a first channel in said surface, said rotor rotable with respect to said stator about said centerpoint of said stator between a load position and an injection position,
said load position defined by said first stator port and said orifice communicating with said first channel, and
said injection position defined by said orifice and a second stator port communicating with said first channel.

* * * * *